(12) United States Patent
Ji et al.

(10) Patent No.: US 11,331,261 B2
(45) Date of Patent: May 17, 2022

(54) TRANSDERMAL DELIVERY COMPLEX USING METAL-ORGANIC FRAMEWORK AND NANOCELLULOSE

(71) Applicant: H&A PHARMACHEM CO., LTD, Gyeonggi-do (KR)

(72) Inventors: Hong Geun Ji, Gyeonggi-do (KR); Young Ah Park, Incheon (KR); Hae In Choi, Incheon (KR); Yu Jin Kang, Gyeonggi-do (KR); Min Hee Kim, Seoul (KR)

(73) Assignee: H&A PHARMACHEM CO., LTD, Gyeonggi-do (KR)

( * ) Notice: Subject to any disclaimer, the term of this patent is extended or adjusted under 35 U.S.C. 154(b) by 0 days.

(21) Appl. No.: 16/769,679

(22) PCT Filed: Dec. 20, 2018

(86) PCT No.: PCT/KR2018/016339
§ 371 (c)(1),
(2) Date: Jun. 4, 2020

(87) PCT Pub. No.: WO2019/125011
PCT Pub. Date: Jun. 27, 2019

(65) Prior Publication Data
US 2020/0375878 A1 Dec. 3, 2020

(30) Foreign Application Priority Data
Dec. 21, 2017 (KR) ........................ 10-2017-0177114

(51) Int. Cl.
*A61K 8/96* (2006.01)
*A61K 8/9789* (2017.01)
*A61K 8/14* (2006.01)
*A61K 8/34* (2006.01)
*A61K 8/55* (2006.01)
*A61K 8/73* (2006.01)
*A61Q 7/00* (2006.01)
*A61Q 17/00* (2006.01)
*A61Q 19/00* (2006.01)
*A61Q 19/02* (2006.01)
*A61Q 19/08* (2006.01)

(52) U.S. Cl.
CPC ............... *A61K 8/965* (2013.01); *A61K 8/14* (2013.01); *A61K 8/342* (2013.01); *A61K 8/553* (2013.01); *A61K 8/731* (2013.01); *A61K 8/9789* (2017.08); *A61Q 7/00* (2013.01); *A61Q 17/00* (2013.01); *A61Q 19/007* (2013.01); *A61Q 19/02* (2013.01); *A61Q 19/08* (2013.01)

(58) Field of Classification Search
CPC .... A41D 13/11; A41D 13/1115; A61K 8/965; A61K 8/96; A61K 8/73
USPC .......................... 422/401, 405, 413
See application file for complete search history.

(56) References Cited

U.S. PATENT DOCUMENTS

| | | | |
|---|---|---|---|
| 4,661,344 A * | 4/1987 | Relenyi ................. | A01N 37/30 424/78.27 |
| 2007/0202038 A1* | 8/2007 | Yaghi ..................... | B01J 20/226 423/702 |
| 2010/0226991 A1 | 9/2010 | Horcajada-Cortes et al. | |
| 2015/0150981 A1* | 6/2015 | Gref ........................ | A61K 47/24 514/777 |
| 2016/0015098 A1* | 1/2016 | Conlon .............. | A41D 13/1192 128/863 |
| 2016/0101192 A1 | 4/2016 | Berthelot et al. | |

FOREIGN PATENT DOCUMENTS

| | | |
|---|---|---|
| CN | 106995531 A | 8/2019 |
| JP | 2011-501739 A | 1/2011 |
| JP | 2016-052620 A | 4/2016 |
| KR | 10-2002-0079150 A | 10/2002 |

OTHER PUBLICATIONS

Zhu et al., "Flexible and Porous Nanocellulose Aerogels with High Loadings of Metal-Organic Framework Particles for Separations Applications." Advanced Materials, vol. 28, Issue 35;p. 7652-7657:published Jun. 30, 2016 (Year: 2016).*
Ludwicka et al., "Chapter 9—Medical and Cosmetic Applications of Bacterial NanoCelllulose." Bacterial Nanocellulose: From Biotechnology to Bio-Economy, 2016, pp. 145-165. (Year: 2016).*
De France, K. J., et al. (2017) "Review of Hydrogels and Aerogels Containing Nanocellulose." *Chemistry of Materials*, 29(11):4609-4631, (Apr. 16, 2017).
Jin, Y. (2016) "Synthesis and Application of Oxidised Cellulose. Thesis for the degree of Doctor of Philosophy." *University of Bath Department of Chemistry*, pp. 1-206.
Thunberg, J. (2015) "Chemical Modification of Electrospun Cellulose Nanofibers. Thesis For The Degree of Doctor of Philosophy." *Department of Chemistry and Chemical Engineering*, Chalmers University of Technology, Göteborg, Sweden 2015, pp. 1-73.
International Search Report issued in International Patent Application No. PCT/KR2018/016339, dated May 24, 2019, with English Translation.
Extended European Search Report from corresponding European Patent Application No. 18892872.5, dated Aug. 20, 2021.

* cited by examiner

*Primary Examiner* — Walter E Webb
(74) *Attorney, Agent, or Firm* — Harness, Dickey & Pierce, P.L.C.

(57) ABSTRACT

The present invention relates to a transdermal delivery complex using a metal-organic framework (MOF) and nanocellulose. In addition, the present invention relates to a cosmetic composition comprising the transdermal delivery complex and a method for preparation of a transdermal delivery complex.

10 Claims, 9 Drawing Sheets

TRANSDERMAL DELIVERY COMPLEX USING METAL-ORGANIC FRAMEWORK AND NANOCELLULOSE

CROSS-REFERENCE TO RELATED APPLICATIONS

This application is a national phase application of PCT Application No. PCT/KR2018/016339, filed on Dec. 20, 2018, which claims priority to Korean Patent Application No. 10-2017-0177114, filed on Dec. 21, 2017. The entire disclosure of the applications identified in this paragraph is incorporated herein by reference.

FIELD

The present invention relates to a composite for transdermal delivery in which a metal-organic framework (MOF) and nanocellulose are used.

In addition, the present invention relates to a cosmetic composition comprising the composite for transdermal delivery.

Furthermore, the present invention relates to a method for preparing the composite for transdermal delivery.

BACKGROUND

To stabilize an active ingredient and increase transdermal efficiency, effort and study for utilizing a transdermal delivery system to functional cosmetics have been actively carried out. Because of developing functional materials, various functionalization methods for imparting higher stability to such materials have been widely studied. Specifically, it is well known that light, heat and oxygen in the air seriously reduce the biological activity of functional materials. As such, there is a need to develop a new transdermal delivery system for stabilizing various active ingredients.

Researches about the synthesis and properties of a substance known as a metal-organic framework (MOF) have been actively conducted. The metal-organic framework is a three-dimensional crystalline porous material formed by coordination of a secondary structural unit containing a metal ion or a metal duster and an organic ligand. Up to now, thousands of metal-organic frameworks have been synthesized with the combination of metal secondary structural units and various organic ligand structures. Compared to conventional porous materials such as zeolite, activated carbon, silica and the like, the surface area of metal-organic frameworks is from 3 times to 7 times higher than that of conventional porous materials, and chemical functionalization is easier. As such, metal-organic frameworks have attracted attention as a new material to replace conventional porous materials.

MOF-5—which is a metal-organic framework synthesized by professor Omar M. Yaghi of the United States in 1999—is the first and representative metal-organic framework produced by coordinating between a 1,4-benzenedicarboxylic acid (BDC) organic ligand and a secondary structural unit of $Zn_4O$. In the same year, the Williams research group in Hong Kong also synthesized a new form of metal-organic framework, HKUST-1, by the combination of 1,3,5-benzenetricarboxylic acid and secondary structural units of $Cu_2(COOR)_4$. In the case of HKUST-1, after synthesis, the solvent is coordinated to the $Cu^{2+}$ metal, and when it is heat-treated under vacuum, an open-metal site (OMS) is formed. As a result, it acts like a Lewis acid and can interact with electron-rich chemical species (Lewis base), thereby making it useful for catalysts, gas separation and storage.

The Yaghi research group in the United States, which synthesized MOF-5, designed and synthesized various MOFs modified from the first reported MOF-5 structure using organic synthesis technology. By adjusting the length of the organic ligand, MOFs having structures similar to MOF-5 but having an enlarged void size were synthesized. In addition, by using organic ligands having various functional groups, various functional groups were successfully introduced into the MOF structure. The tailor-made synthesis strategy—in which the desired properties can be controlled from the design stage—can be said to be a very unique advantage, making MOF materials different from other porous materials.

The Ferey research group in France has been researching Cr- and Fe-based carboxylate MOFs and synthesizing the MIL series, and MIL-53 (trade name: Basolite A100), a coordination compound of Al and benzenetricarboxylate (H3BTC) has been studied as a catalyst and adsorbent. In addition, MIL-101 has been reported as a porous material with a large surface area of up to 5,900 $m^2/g$.

With the development of technologies in organic synthesis, organic ligands of various designs have been synthesized, and thousands of MOFs and various properties thereof have been reported by a combination of various metals and metal-clusters. The Hupp research group at Northwestern University in the United States has extended the length of organic ligands to synthesize a new form of MOF, Nu-110. A new ligand was designed through an experimental method and a computational chemical method, and Nu-110 was synthesized by reacting the new ligand with copper nitrate. The synthesized Nu-110 MOF has the largest surface area among the existing MOF materials, and its surface area is 7,100 $m^2/g$, which is a huge surface area that can cover all of an American football field with 1 g of MOE This high surface area can serve as a great advantage when using MOF as a storage and separation of gases or as an energy storage. In the drug delivery system, it is a problem that the drug is rapidly decomposed before arriving at the target body tissue and its activity is lowered. Therefore, studies are being conducted to deliver drugs using a carrier to increase drug activity. In the case of using a carrier, it not only increases the stability of the drug, but also reduces the toxicity of the drug and increases the efficiency of the drug. As necessary conditions of the carrier for efficient drug delivery, a high loading amount, prevention of burst phenomenon and regulation of decomposition of the carrier are required. The nano-carriers reported to date include liposomes, nanoemulsions, nanoparticles, micelles, silica, etc., but these carriers did not meet the necessary conditions previously recited. According to the results of M. Vallet-Regi's research team, the storage capacity of the drug being loaded is reduced, especially in the case of silica, Therefore, MOF has been suggested as a solution to this problem. MOF is a material that combines the advantages of large pore volume, regular porosity and easy control of pore size. In this context, adjusting the pore structure and chemical functionality of the MOF can compensate for the shortcomings of currently used carriers, thereby realizing high drug loading, carrier-drug interactions and adequate release rates.

The Patricia Horcajada research team tried to apply the carrier as a carrier that can improve the drug-loading and carrier-drug interaction by adjusting the structure and porosity of the porous organo-metal structure. The research team used porous iron-carboxylate MOFs as nano-sized carriers to encapsulate drugs with different polarities, sizes and various functional groups. The iron-carboxylate MOFs used herein have advantages as carriers because they are non-toxic and biocompatible. In addition, the research team used water or ethanol instead of organic solvents in the process of immersing the MOFs in a solution in which each drug was dissolved to increase the potential for biomedical application.

Cellulose is a natural polymer composed of β(1-4) linkages of glucose, and does not exist independently as a single molecule in the plant cell wall, but exists as a layered hierarchical structure. Cellulose is the most abundant natural polymer material in nature and can be obtained mainly from wood and non-wood plant raw materials or synthesized through bacteria. In the case of wood, the cellulose content occupies about 40-55% of the total components, and by removing a significant amount of lignin and hemicellulose through a pulping process, it is possible to obtain pulp fibers which are of about 80% cellulose. Microfibers are formed through hydrogen bonding between cellulose chains, and several microfibers are bundled together to form macrofibers, from which fibers are formed. Cellulose has high strength, flexibility and strong hydrophilicity, and has properties such as biocompatibility and biodegradability, and thus has been studied and used in various fields such as paper and clothing.

Nanocellulose is a nano-structured cellulose. As nanotechnology began to draw attention in the scientific community, research on "cellulose nanofibers"—which are celluloses on a nanoscale—began to be actively conducted in the cellulose field. Cellulose nanofiber refers to a nano-level cellulose fiber having at least one dimension of less than 100 nm in the width or length of the fiber, and is generally manufactured by a chemical treatment method that is acid hydrolysis, a biological treatment method and a mechanical treatment method.

As a method of manufacturing cellulose nanofibers, cellulose nanofibers manufactured by a chemical treatment method through acid hydrolysis are called cellulose nanocrystals (CNC). Cellulose is composed of a crystalline region and a non-crystalline region. When the amorphous region is decomposed by acid treatment and a particle shape composed of the crystalline region is obtained, this is called cellulose nanocrystal. In general, this has disadvantages in that the manufacturing yield is very low and the manufacturing process including the acid removal process is complicated. Cellulose nanofibers produced by biological methods are also called bacterial celluloses because they are synthesized from bacteria such as *Acetobacter xylinum*. While a biological method has the advantage of obtaining high purity cellulose, it has the disadvantage that the production rate is very low. Cellulose nanofibers can be produced through mechanical processing such as high pressure homogenizing, microfluidizing and grinding. When a single fiber or a combination of several microfibers is obtained from cellulose fibers by mechanical treatment, these cellulose nanofibers are called cellulose nanofibrils (CNF).

Nanocellulose (cellulose nanocrystals [CNC] or cellulose nanofibrils [CNF]) has the potential to be applied to a very wide range of fields due to physical and chemical properties such as mechanical properties, film-forming properties, viscosity and high surface area.

SUMMARY

Technical Problem

Therefore, the technical problem of the present invention is the provision of a new composite for transdermal delivery which can efficiently deliver an active ingredient into the skin in a stable manner.

In addition, another technical problem of the present invention is the provision of a cosmetic composition comprising the composite for transdermal delivery.

Furthermore, still another technical problem of the present invention is the provision of a method for preparing the composite for transdermal delivery.

Solution to Problem

To solve the above technical problem, the present invention provides a composite for transdermal delivery comprising a metal-organic framework and nanocellulose.

In addition, the present invention provides a cosmetic composition comprising the composite for transdermal delivery.

Furthermore, the present invention provides a method for preparing a composite for transdermal delivery comprising: i) adding a nanocellulose solution to a metal-organic framework solution; ii) treating the solution obtained in step (i) by stirring or sonication to form a composite; and iii) drying the composite obtained in step (ii).

The present invention is described in detail hereinafter.

According to one aspect to the present invention, there is provided a composite for transdermal delivery comprising a metal-organic framework and nanocellulose.

In the present invention, as one ingredient of the composite for transdermal delivery, a metal-organic framework (MOF) is comprised.

A metal-organic framework is a three-dimensional crystalline porous material formed by coordination of a secondary structural unit containing a metal ion or a metal duster and an organic ligand. In the present invention, the metal-organic framework is preferably a zeolite imidazolate framework (ZIF). The zeolite imidazolate framework is composed of transition metal ion (e.g., Fe, Co, Cu or Zn) connected by an imidazolate linker.

Figure 1:
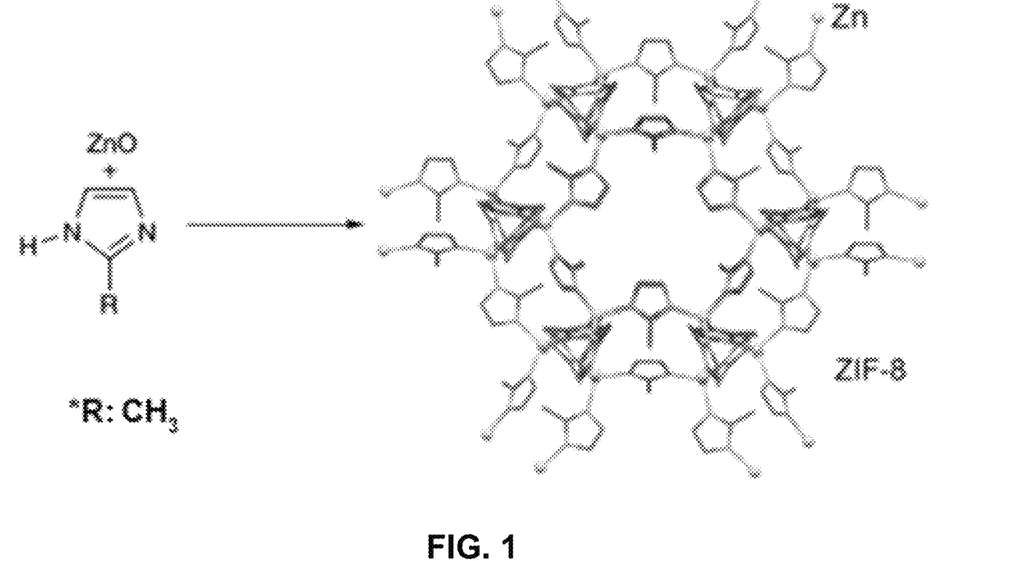
FIG. 1 is a schematic diagram representing the structure of ZIF-8.
Figure 2:
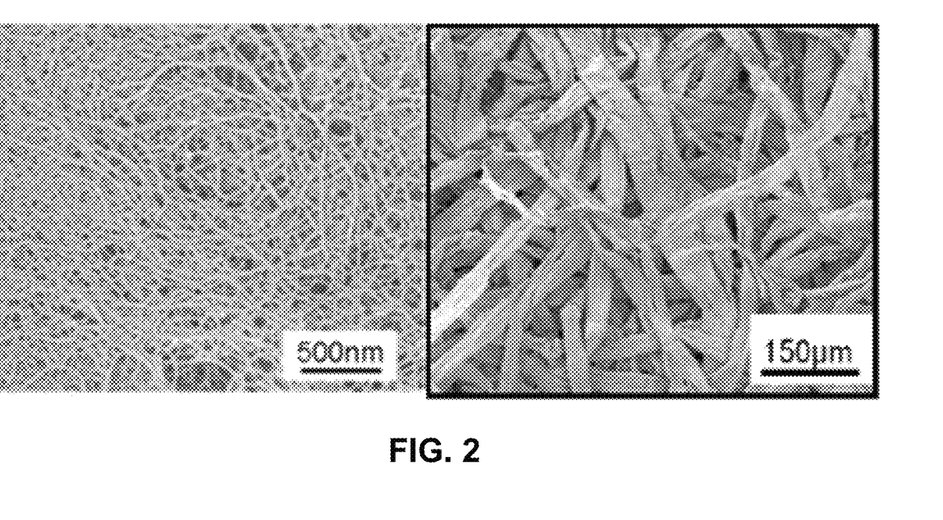
FIG. 2 is scanning electron microscopy photographs of nanocellulose.

In the present invention, the zeolite imidazolate framework is preferably ZIF-8. The ZIF-8 has a structure in which four (4) imidazoles are coordinated to zinc (Zn) ions (FIG. 1).

In the present invention, as one ingredient of the composite for transdermal delivery, nanocellulose is comprised. In the present invention, nanocellulose forms a composite with a metal-organic framework to improve the transdermal delivery effect and impart the stability to the transdermal delivery system.

In the present invention, preferably 0.01 to 20 parts by weight of the nanocellulose forms a composite, based on 10 parts by weight of the metal-organic framework. In one embodiment of the present invention, an imine group of the ZIF-8 is combined with the nanocellulose.

According to one embodiment of the present invention, the composite for transdermal delivery may further comprise an active ingredient. In the present invention, there is no special limitation according to an active ingredient. In the present invention, examples of an active ingredient include, but are not limited to, one or more selected from a moisturizer, a whitening agent, an anti-wrinkle agent, a UV blocking agent, a hair growth promoter, vitamin or a derivative thereof, amino acid or peptide, an anti-inflammatory agent, an acne therapeutic agent, a microbicide, female hormone, a keratolytic agent and a natural product. In addition, cosmetic ingredients such as oils, waxes, butters, paraffin, higher fatty acids such as stearic acid, esters such as cetyl ethylhexanoate, and silicones may also be used as an active ingredient.

Examples of moisturizer include, but are not limited to, creatine, polyglutamic acid, sodium lactate, hydroproline, 2-pyrrolidone-5-carboxyclic acid sodium salt, hyaluronic acid, sodium hyaluronate, ceramide, phytosteryl, cholesterol, sitosterol, pullulan and proteoglycan. Examples of whitening agent include, but are not limited to, arbutin and a derivative thereof, kojic acid, bisabolol, niacinamide, vitamin C and a derivative thereof, placenta and allantoin. Examples of anti-wrinkle agent include, but are not limited to, retinol, retinol derivative, adenosine, licorice extract, red ginseng extract and ginseng extract. Examples of UV blocking agent include, but are not limited to, benzophenone derivative, para-aminobenzoic acid derivative, methoxycinnamic acid derivative and salicylic acid derivative. There is no special limitation to a hair growth promoter, but it may be preferably a blood circulation promoter and/or a hair follicle stimulant. Examples of blood circulation promoter include, but are not limited to, the extract of *Swertia japonica* Makino, cepharanthin, vitamin E and a derivative thereof and gamma-oryzanol, and examples of hair follicle stimulant include, but are not limited to, *capsicum* tincture, ginger tincture, cantharides tincture and nicotinic acid benzyl ester. Examples of vitamin or a derivative thereof include, but are not limited to, vitamin A (retinol) and a derivative thereof, vitamin B1, vitamin B2, vitamin B6, vitamin E and derivatives thereof, vitamin D, vitamin H, vitamin K, pantothenic acid and derivatives thereof, biotin, panthenol, coenzyme $Q_{10}$ and idebenone. Examples of amino acid or peptide include, but are not limited to, cysteine, methionine, serine, lysine, tryptophan, amino acid extract, epidermal growth factor (EGF), insulin-like growth factor (IGF), fibroblast growth factor (FGF), copper tripeptide-1, tripeptide-29, tripeptide-1, acetyl hexapeptide-8, nicotinoyl tripeptide-35, hexapeptide-12, hexapeptide-9, palmitoyl pentapeptide-4, palmitoyl tetrapeptide-7, palmitoyl tripeptide-29, palmitoyl tripeptide-1, nonapeptide-7, tripeptide-10 citrulline, sh-polypeptide-15, palmitoyl tripeptide-5, diaminopropionoyl tripeptide-33 and r-spider polypeptide-1. Examples of anti-inflammatory agent include, but are not limited to, beta-glycyrrhetinic acid, glycyrrhetinic acid derivative, aminocaproic acid, hydrocortisone, β-glucan and licorice. Examples of acne therapeutic agent include, but are not limited to, estradiol, estrogen, ethinyl estradiol, triclosan and azelaic acid. Examples of microbicide include, but are not limited to, benzalkonium chloride, benzethonium chloride and halocalban. There is no special limitation to female hormone, but it may be preferably estrogen. As estrogen, it may be preferably estradiol, ethinyl estradiol or isoflavone which is a phytoestrogen. Examples of keratolytic agent include, but are not limited to, sulfur, salicylic acid, AHA, BHA and resorcin. Examples of the extract of natural product or an ingredient obtained therefrom include, but are not limited to, the extract of Japanese witch-hazel, *Lamium album* var. barbatum, *Hedyotis diffuse, Rheum palmatum*, licorice, aloe, chamomile, rose hip, horse chestnut, ginseng, *Luffa aegyptiaca*, cucumber, laver, sea mustard, *Dioscorea batatas*, snail and fruit of *Dioscorea polystachya*, or hinokitiol and beta-carotene. In addition, yeast extract, collagen, elastin, *Centella asiatica* extract, aluminum sucrose octasulfate, DHA, EPA, flavor ingredient and the like may be used.

According to another aspect of the present invention, there is provided a cosmetic composition comprising the composite for transdermal delivery of the present invention. In the present invention, the cosmetic composition may be formulated to toner, lotion, body lotion, cream, essence and the like, but is not limited thereto.

The cosmetic composition comprises preferably 1 to 60% by weight, more preferably 2 to 50% by weight of the composite for transdermal delivery according to the present invention. In the present invention, if the cosmetic composition comprises the composite for transdermal delivery in an amount of less than 1% by weight, the effect according to an active ingredient may be weak, and if the amount of the composite for transdermal delivery is greater than 60% by weight, it may be economically undesirable since increasing the effect according to an active ingredient commensurately with the added amount would not be expected.

According to still another aspect of the present invention, there is provided a method for preparing a composite for transdermal delivery comprising: i) adding a nanocellulose solution to a metal-organic framework solution; ii) treating the solution obtained in step (i) by stirring or sonication to form a composite; and iii) drying the composite obtained in step (ii).

In step (i) of the preparation method, the metal-organic framework solution may be obtained by dissolving a metal-organic framework in a solvent—e.g., distilled water. The metal-organic framework is preferably a zeolite imidazolate framework (ZIF). In the present invention, the zeolite imidazolate framework is preferably ZIF-8.

In one embodiment of the present invention, ZIF-8 may be prepared by adding dropwise and stirring 2-methylimidazole solution to zinc nitrate hexahydrate solution.

In one embodiment of the present invention, the nanocellulose solution may comprise nanocellulose in a concentration of 5 to 20% by weight.

In step (ii) of the preparation method, when the solution obtained by adding the nanocellulose solution to the metal-organic framework solution is treated by stirring or sonication, the nanocellulose and the metal-organic framework are combined to form a composite. In one embodiment of the present invention, an imine group of the ZIF-8 is combined with the nanocellulose.

In step (iii) of the preparation method, drying of the prepared composite may be carried out, for example, by high-temperature vacuum drying at 60° C. or higher, or freeze-drying. In one embodiment of the present invention, after the drying of the step (iii), a step of washing the prepared composite may be further carried out. The washing of the composite may be carried out, for example, by the use of ethanol.

Effects of the Invention

A composite for transdermal delivery according to the present invention can show excellent efficacy even with a small amount of an active ingredient for a long time by efficiently transferring an active ingredient into the skin in a very stable form.

DETAILED DESCRIPTION

Hereinafter, the present invention is explained in more detail with the following examples. However, it must be understood that the protection scope of the present invention is not limited to the examples.

Preparation Example: Preparation OF ZIF-8

Preparation Example 1-1: Preparation of Zinc Nitrate Hexahydrate Solution 0.4 g of zinc nitrate hexahydrate was completely dissolved in 1.6 g of $H_2O$. At this time, $H_2O$ was used after adjusting to pH 8.0 using NaOH, and sonication was carried out for 5 minutes for complete dissolution. Then, 8 ml of non-ionized $H_2O$ was added and stirred at 300 rpm for 30 minutes.

Preparation Example 1-2: Preparation of 2-methylimidazole Solution 4.0 g of 2-ethylimidazole was completely dissolved in 16.0 g of non-ionized $H_2O$. At this time, sonication was carried out for 30 minutes or more for complete dissolution.

Preparation Example 1-3: Synthesis of ZIF-8

The 2-methylimidazole solution of Preparation Example 1-2 was added dropwise to the zinc nitrate hexahydrate solution of Preparation Example 1-1, and the mixture was stirred at 300 rpm for 30 minutes. Through this process, imidazole bridges were formed in $Zn^{2+}$, and ligands were synthesized to form ZIF-8. The obtained ZIF-8 was washed and dried at 70° C. for 7 hours and 30 minutes.

Preparation Example 1-4: Washing of ZIF-8

After centrifugation twice using distilled water, washing was carried out by centrifugation twice using ethanol. At this time, the conditions of centrifugation were carried out at 4,000 rpm for 15 minutes Universal 320/Germany).

Example 1: Preparation of Composite Via Stirring and High-Temperature Vacuum Drying The 2-methylimidazole solution of Preparation Example 1-2 was added dropwise to the zinc nitrate hexahydrate solution of Preparation Example 1-1, and the mixture was stirred at 300 rpm for 15 minutes. After stirring, nanocellulose (CelluForce NCC™, CelluForce Inc., Canada) was added according to the composition recited in Table 1, respectively, followed by stirring at 300 rpm for 15 minutes. After washing, vacuum drying at 70° C. for 7 hours and 30 minutes was carried out.

TABLE 1

| | Example 1-1 | Example 1-2 | Example 1-3 | Example 1-4 | Example 1-5 |
|---|---|---|---|---|---|
| ZIF-8 solution | 29 ml | 27 ml | 25 ml | 23 ml | 20 ml |

TABLE 1-continued

| | Example 1-1 | Example 1-2 | Example 1-3 | Example 1-4 | Example 1-5 |
|---|---|---|---|---|---|
| 10% nano-cellulose solution | 1 ml | 3 ml | 5 ml | 7 ml | 10 ml |

Example 2: Preparation of Composite Via Sonication and High-Temperature Vacuum Drying The 2-methylimidazole solution of Preparation Example 1-2 was added to the zinc nitrate hexahydrate solution of Preparation Example 1-1, and sonication was carried out at 25° C. for 15 minutes. After sonication, nanocellulose was added according to the composition recited in Table 2, respectively, and sonication was then carried out at 25° C. for 15 minutes. After washing, vacuum drying at 70° C. for 7 hours and 30 minutes was carried out.

TABLE 2

| | Example 2-1 | Example 2-2 | Example 2-3 | Example 2-4 | Example 2-5 |
|---|---|---|---|---|---|
| ZIF-8 solution | 29 ml | 27 ml | 25 ml | 23 ml | 20 ml |
| 10% nano-cellulose solution | 1 ml | 3 ml | 5 ml | 7 ml | 10 ml |

Example 3: Preparation of Composite Via Sonication and Freeze-Drying

The 2-methylimidazole solution of Preparation Example 1-2 was added to the zinc nitrate hexahydrate solution of Preparation Example 1-1, and sonication was carried out at 25° C. for 15 minutes. After sonication, nanocellulose was added according to the composition recited in Table 3, respectively, and sonication was then carried out at 25° C. for 15 minutes. After washing, the obtained composites were frozen at −120° C. for at least 3 hours, and then dried for 2 days.

TABLE 3

| | Example 3-1 | Example 3-2 | Example 3-3 | Example 3-4 | Example 3-5 |
|---|---|---|---|---|---|
| ZIF-8 solution | 29 ml | 27 ml | 25 ml | 23 ml | 20 ml |
| 10% nano-cellulose solution | 1 ml | 3 ml | 5 ml | 7 ml | 10 ml |

Figure 3:
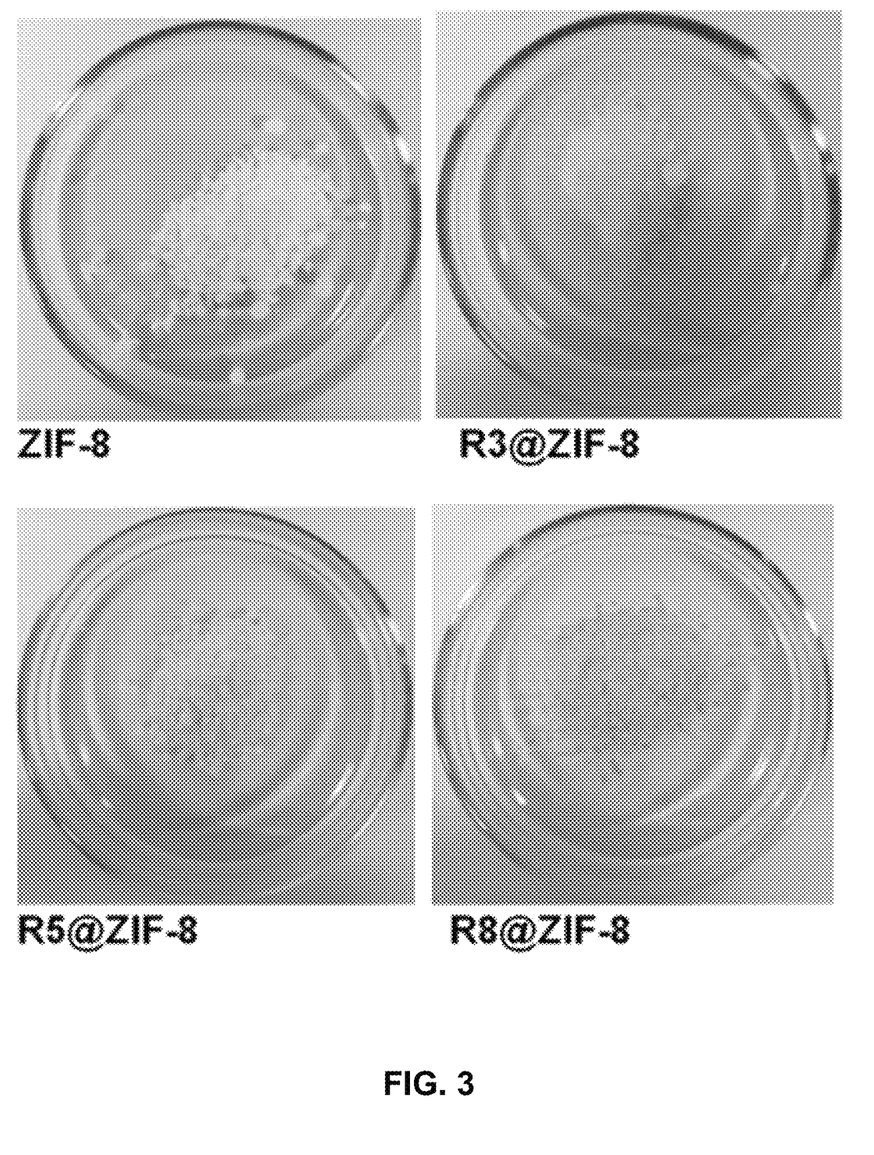
FIG. 3 is photographs of the prepared ZIF-8 and ZIF-8-nanocellulose composite comprising retinol.

Example 4: Preparation of ZIF-8-Nanocellulose Composite Containing Retinol 10 g of ZIF-8, 6 g of nanocellulose, 3, 5 or 8 g of retinol and 38.5 g of water were mixed, and the mixture was treated with an ultrasonic mixer, washed and then vacuum dried at 70° C. for 7 hours and 30 minutes. As can be seen from FIG. 3, it can be known that as the retinol content increases, the color becomes darker. (Hereinafter, the composites manufactured with 3, 5 or 8 g of retinol were referred to as "R3@ZIF-8," "R5@ZIF-8" and "R8@ZIF-8" respectively.)

Example 5: Preparation of ZIF-8-Nanocellulose Composite Containing Arbutin 10 g of ZIF-8, 8 g of nanocellulose, 10 g of arbutin and 72 g of water were mixed, and the mixture was treated with an ultrasonic mixer, washed and then freeze-dried.

Example 6: Preparation of ZIF-8-Nanocellulose Composite Containing Plant Natural Product A composite was prepared by the same method as described in Example 4 with the constitutional composition of Table 4.

TABLE 4

| Ingredient | Content (part by weight) |
|---|---|
| ZIF-8 | 5 |
| Nanocellulose | 1 |
| Cucumber extract | 20 |
| Distilled water | 18.5 |

Example 7: Preparation of ZIF-8-Nanocellulose Composite Containing Marine Natural Product A composite was prepared by the same method as described in Example 4 with the constitutional composition of Table 5.

TABLE 5

| Ingredient | Content (part by weight) |
|---|---|
| ZIF-8 | 8 |
| Nanocellulose | 0.5 |
| Sea mustard extract | 20 |
| Distilled water | 22 |

Example 8: Preparation of ZIF-8-Nanocellulose Composite Containing Oil

A composite was prepared by the same method as described in Example 4 with the constitutional composition of Table 6.

TABLE 6

| Ingredient | Content (part by weight) |
|---|---|
| ZIF-8 | 10 |
| Nanocellulose | 5 |
| Olive oil | 1 |
| *Camellia* oil | 1 |
| *Macadamia* nut oil | 2 |
| Castor oil | 2 |
| Sunflower oil | 2 |
| Jojoba oil | 2 |
| Almond oil | 0.5 |
| Meadowfoam seed oil | 2 |
| Argan oil | 2 |
| Distilled water | 42 |

Example 9: Preparation of ZIF-8-Nanocellulose Composite Containing Wax

A composite was prepared by the same method as described in Example 4 with the constitutional composition of Table 7.

TABLE 7

| Ingredient | Content (part by weight) |
|---|---|
| ZIF-8 | 8 |
| Nanocellulose | 2 |
| Beeswax | 5 |
| Candelilla wax | 5 |
| Distilled water | 35 |

Example 10: Preparation of ZIF-8-Nanocellulose Composite Containing Butter

A composite was prepared by the same method as described in Example 4 with the constitutional composition of Table 8.

TABLE 8

| Ingredient | Content (part by weight) |
|---|---|
| ZIF-8 | 15 |
| Nanocellulose | 3 |
| Shea butter | 1 |
| Mango butter | 5 |
| Green tea butter | 1 |
| Distilled water | 47 |

Example 11: Preparation of ZIF-8-Nanocellulose Composite Containing Paraffin

A composite was prepared by the same method as described in Example 4 with the constitutional composition of Table 9.

TABLE 9

| Ingredient | Content (part by weight) |
|---|---|
| ZIF-8 | 20 |
| Nanocellulose | 10 |
| Liquid paraffin | 20 |
| Distilled water | 60 |

Example 12: Preparation of ZIF-8-Nanocellulose Composite Containing Higher Fatty Acid A composite was prepared by the same method as described in Example 4 with the constitutional composition of Table 10.

TABLE 10

| Ingredient | Content (part by weight) |
|---|---|
| ZIF-8 | 10 |
| Nanocellulose | 0.5 |
| Palmitic acid | 10 |
| Distilled water | 33 |

Example 13: Preparation of ZIF-8-Nanocellulose Composite Containing Ester

A composite was prepared by the same method as described in Example 4 with the constitutional composition of Table 11.

TABLE 11

| Ingredient | Content (part by weight) |
|---|---|
| ZIF-8 | 13 |
| Nanocellulose | 1.5 |
| Cetyl ethylhexanoate | 20 |
| Distilled water | 49 |

Example 14: Preparation of ZIF-8-Nanocellulose Composite Containing Silicone

A composite was prepared by the same method as described in Example 4 with the constitutional composition of Table 12.

TABLE 12

| Ingredient | Content (part by weight) |
| --- | --- |
| ZIF-8 | 30 |
| Nanocellulose | 10 |
| Dimethicone 6CS | 20 |
| Distilled water | 65 |

Example 15: Preparation of ZIF-8-Nanocellulose Composite Containing Moisturizer

A composite was prepared by the same method as described in Example 4 with the constitutional composition of Table 13.

TABLE 13

| Ingredient | Content (part by weight) |
| --- | --- |
| ZIF-8 | 30 |
| Nanocellulose | 15 |
| Ceramide | 5 |
| Hyaluronic acid | 0.5 |
| Polyglutamic acid | 0.1 |
| Distilled water | 73 |

Example 16: Preparation of ZIF-8-Nanocellulose Composite Containing Whitening Agent A composite was prepared by the same method as described in Example 4 with the constitutional composition of Table 14.

TABLE 14

| Ingredient | Content (part by weight) |
| --- | --- |
| ZIF-8 | 16 |
| Nanocellulose | 0.5 |
| Arbutin | 10 |
| Distilled water | 55 |

Example 17: Preparation of ZIF-8-Nanocellulose Composite Containing UV Blocking Agent A composite was prepared by the same method as described in Example 4 with the constitutional composition of Table 15.

TABLE 15

| Ingredient | Content (part by weight) |
| --- | --- |
| ZIF-8 | 20 |
| Nanocellulose | 1.5 |
| Octyl methoxycinnamate | 15 |
| Distilled water | 58 |

Example 18: Preparation of ZIF-8-Nanocellulose Composite Containing Vitamin

A composite was prepared by the same method as described in Example 4 with the constitutional composition of Table 16.

TABLE 16

| Ingredient | Content (part by weight) |
| --- | --- |
| ZIF-8 | 30 |
| Nanocellulose | 10 |
| Vitamin E (tocopherol) | 15 |
| Distilled water | 80 |

Example 19: Preparation of ZIF-8-Nanocellulose Composite Containing Amino Acid

A composite was prepared by the same method as described in Example 4 with the constitutional composition of Table 17.

TABLE 17

| Ingredient | Content (part by weight) |
| --- | --- |
| ZIF-8 | 20 |
| Nanocellulose | 0.1 |
| Epidermal growth factor (EGF) | 0.01 |
| Insulin-like growth factor (IGF) | 0.0001 |
| Distilled water | 58 |

Example 20: Preparation of ZIF-8-Nanocellulose Composite Containing Peptide

A composite was prepared by the same method as described in Example 4 with the constitutional composition of Table 18.

TABLE 18

| Ingredient | Content (part by weight) |
| --- | --- |
| ZIF-8 | 30 |
| Nanocellulose | 20 |
| Palmitoyl pentapeptide-3 | 0.0001 |
| Hexapeptide-9 | 0.001 |
| Palmitoyl tetrapeptide-7 | 0.00001 |
| Nonapeptide-7 | 0.0001 |
| Dipeptide-8 | 0.001 |
| Distilled water | 90 |

Example 21: Preparation of ZIF-8-Nanocellulose Composite Containing Anti-Inflammatory Agent A composite was prepared by the same method as described in Example 4 with the constitutional composition of Table 19.

TABLE 19

| Ingredient | Content (part by weight) |
| --- | --- |
| ZIF-8 | 10 |
| Nanocellulose | 1.5 |
| Hydrocortisone | 5 |
| Distilled water | 46 |

Example 22: Preparation of ZIF-8-Nanocellulose Composite Containing Acne Therapeutic Agent A composite was prepared by the same method as described in Example 4 with the constitutional composition of Table 20.

TABLE 20

| Ingredient | Content (part by weight) |
| --- | --- |
| ZIF-8 | 4 |
| Nanocellulose | 0.5 |
| Azelaic acid | 10 |
| Distilled water | 38 |

Example 23: Preparation of ZIF-8-Nanocellulose Composite Containing Microbicide

A composite was prepared by the same method as described in Example 4 with the constitutional composition of Table 21.

TABLE 21

| Ingredient | Content (part by weight) |
| --- | --- |
| ZIF-8 | 30 |
| Nanocellulose | 15 |
| Halocalban | 20 |
| Distilled water | 77 |

Experimental Example 1: Measurement of Particle Size Distribution

Figure 4:
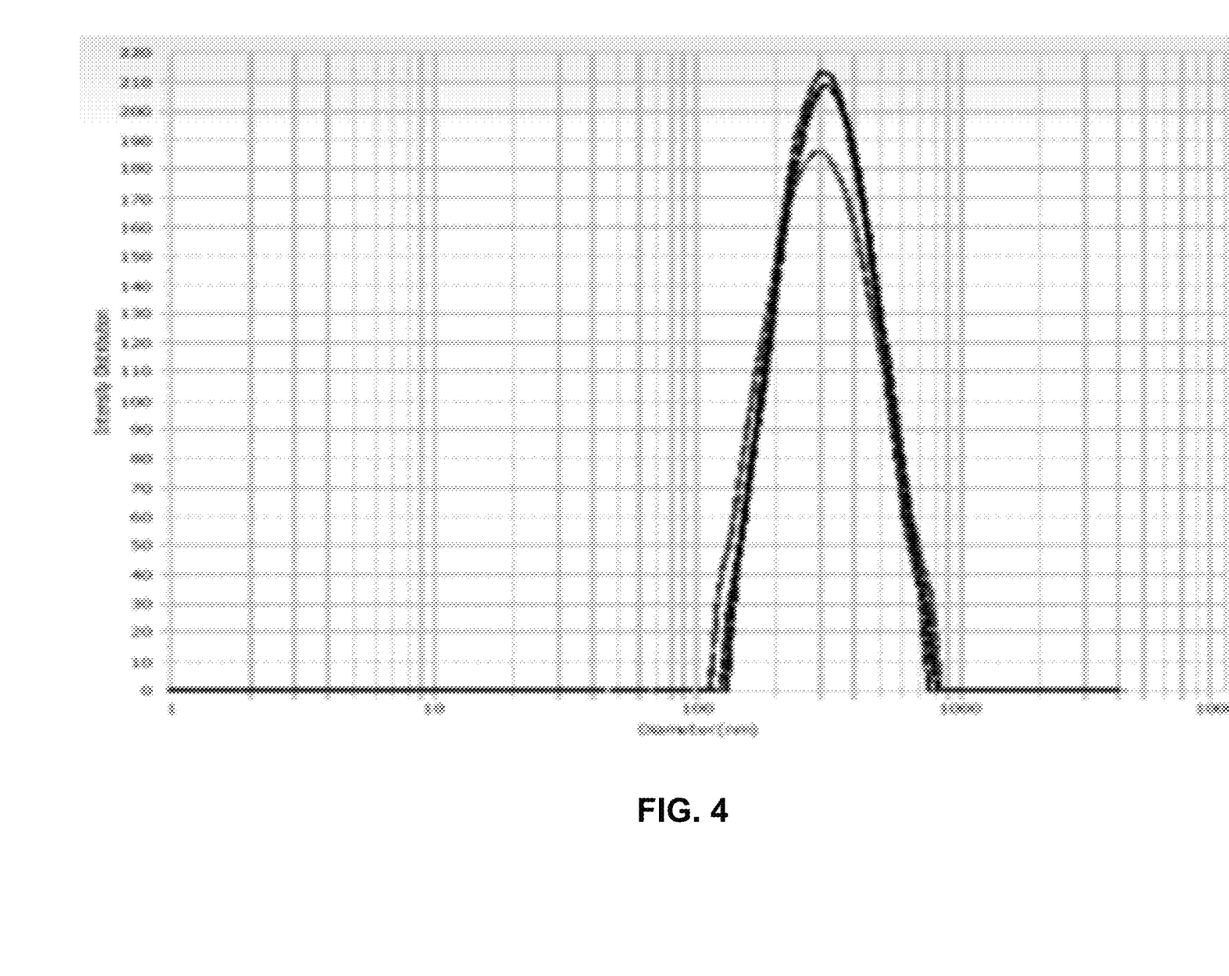
FIG. 4 is a result of measuring the diameter of the ZIF-8-nanocellulose composite by the use of Photal ELS-Z.

The particle size distribution of the ZIF-8-nanocellulose composite prepared in Example 1-2 was measured by the use of Photal, ELS-Z, and the result is represented in FIG. 4. From the result of the measurement, it can be known that the average particle size of the composite is 281.8 nm.

Experimental Example 2: Cryo-Electron Microscopy

Figure 5:
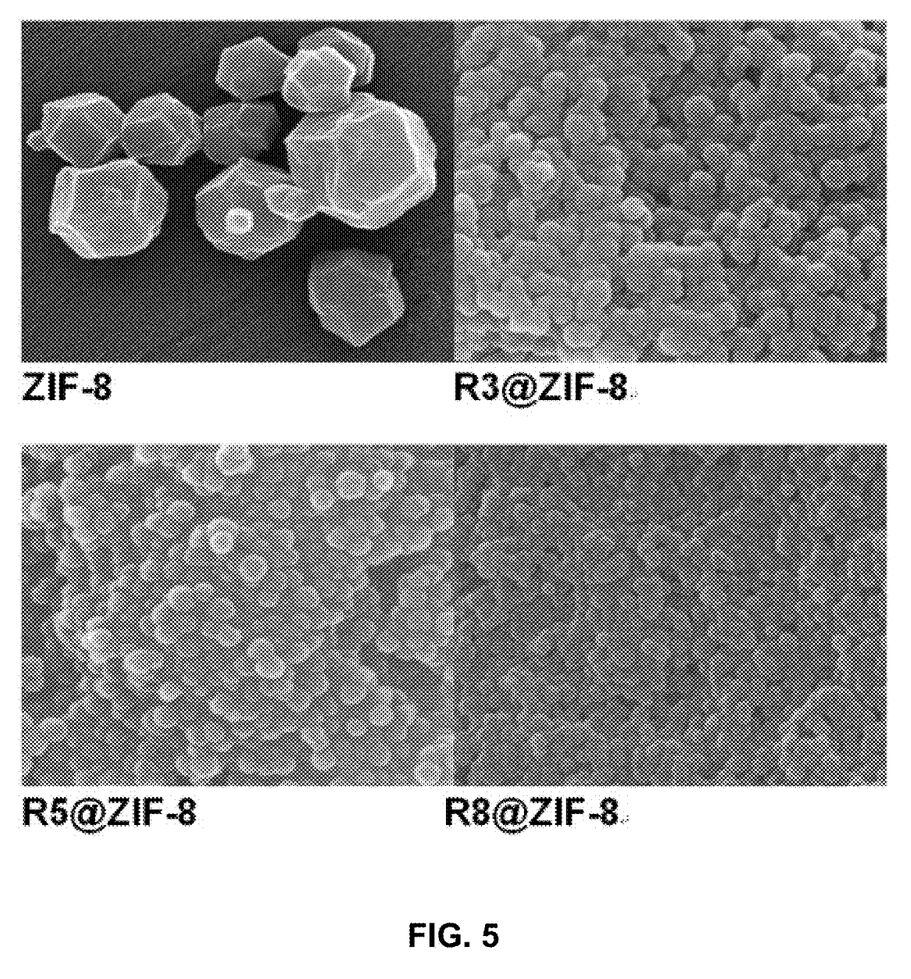
FIG. 5 is a cryo-electron microscopy photographs of the ZIF-8 and ZIF-8-nanocellulose composite containing retinol.

Photographs of the ZIF-8 prepared in the Preparation Example and the ZIF-8-nanocellulose composite containing retinol prepared in Example 4 were taken. Due to very fine particle size, it was impossible to take photographs by a general optical microscope. Therefore, cryo-electron microscopy photographs (JEM 1010, JEOL Ltd., Japan) were taken (FIG. 5).

Experimental Example 3: NMR Test

Figure 6:
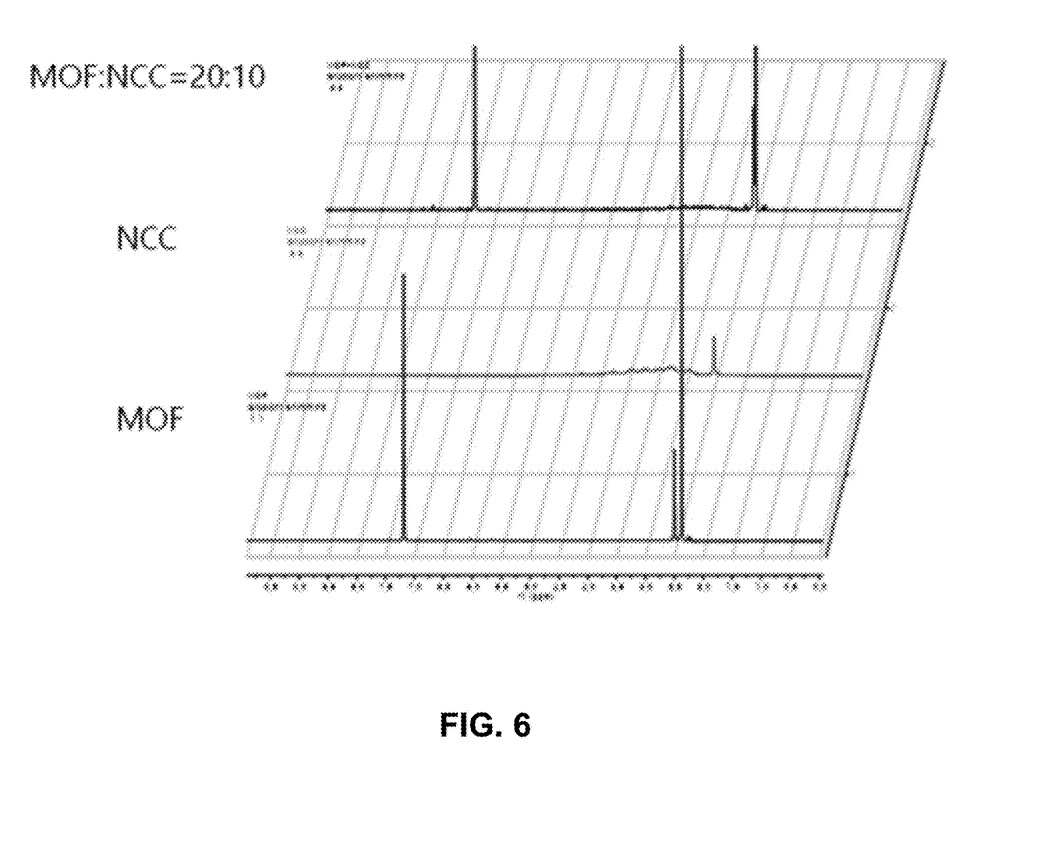
FIG. 6 is a result of measuring H-NMR of the ZIF-8-nanocellulose composite prepared in Example 1-5.

The ZIF-8-nanocellulose composite prepared in Example 1-5 was measured by H-NMR (FIG. 6).

Figure 7:
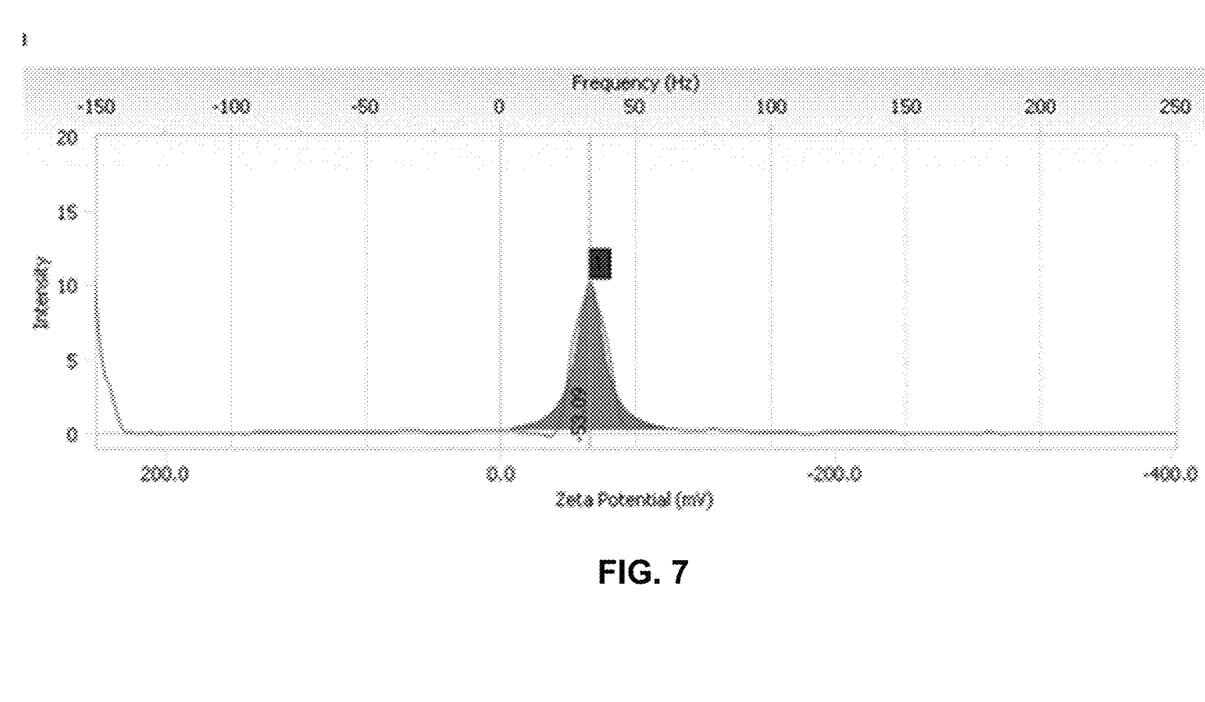
FIG. 7 is a result of measuring zeta potential by the use of Photal ELS-Z to measure the stability of the ZIF-8-nanocellulose composite.

Experimental Example 4: Measurement of Stability of ZIF-8-Nanocellulose Composite To measure the stability of the ZIF-8-nanocellulose composite prepared in Example 1-2, zeta potential was measured by the use of Photal, ELS-Z, and the result is represented in FIG. 7. From the result of the measurement, it can be known that the potential of particle is −53.09 mV, and the composite is stable.

Figure 8:
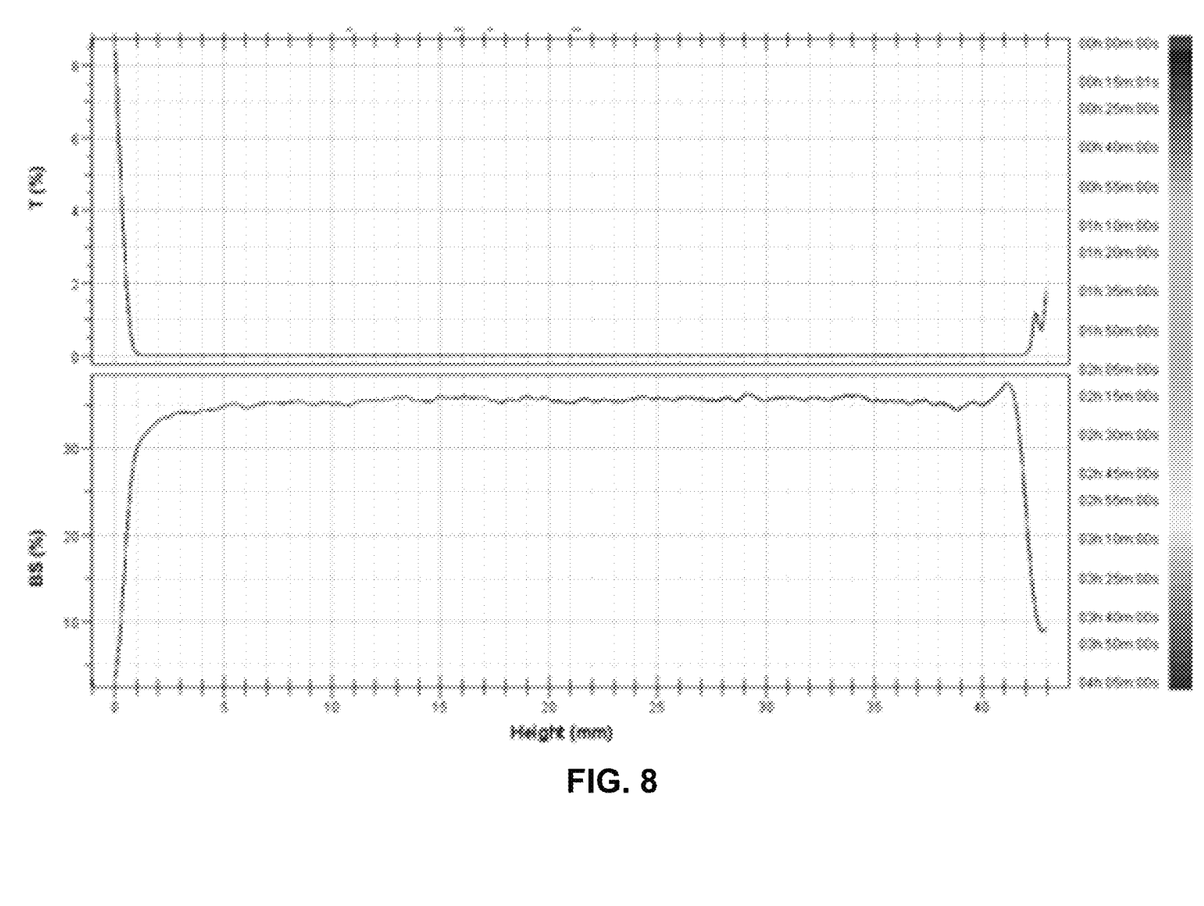
FIG. 8 is a result of measuring the stability of the ZIF-8-nanocellulose composite by the use of Turbiscan.

Experimental Example 5: Measurement of Stability of ZIF-8-Nanocellulose Composite The stability of the ZIF-8-nanocellulose composite prepared in Example 1-2 was measured by the use of Turbiscan. As a result, the stability of the composite was confirmed (FIG. 8).

Experimental Example 6: X-Ray Powder Diffraction Test

Figure 9:
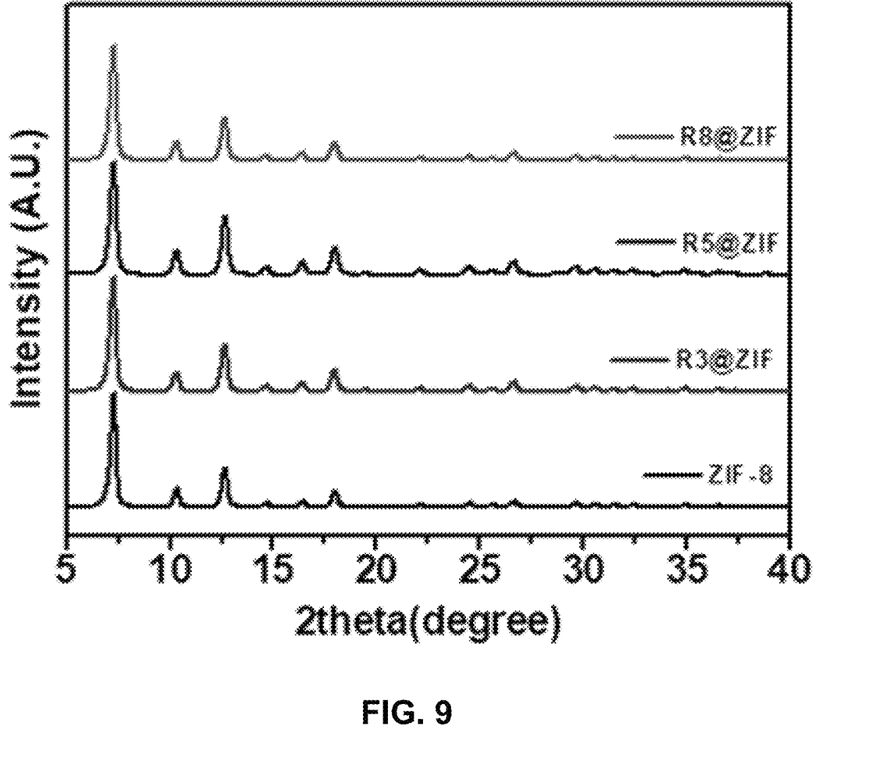
FIG. 9 is X-ray powder diffraction (XRD) spectrums of the ZIF-8 and ZIF-8-nanocellulose composite containing retinol.

A powder X-ray powder diffraction (XRD) test of the ZIF-8 prepared in the Preparation Example and the ZIF-8-nanocellulose composite containing retinol prepared in Example 4 was carried out, and the results are represented in FIG. 9. As can be seen from FIG. 9, it can be known that each of the composites were synthesized well as constant peaks appear.

Experimental Example 7: NMR Test

Figure 10:
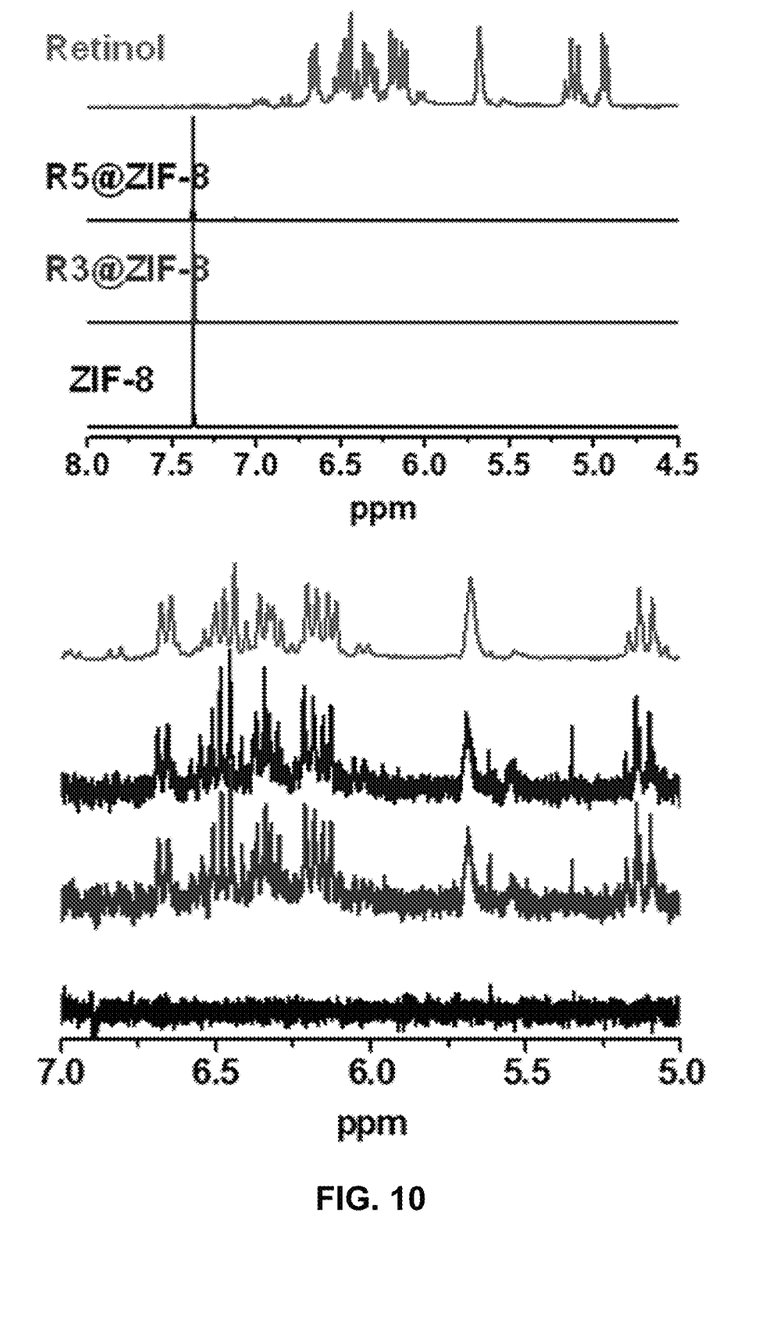
FIG. 10 is results of measuring NMR of the ZIF-8 and ZIF-8-nanocellulose composite containing retinol.

From the results of NMR measurement of the ZIF-8 prepared in the Preparation Example and the ZIF-8-nanocellulose composite containing retinal prepared in Example 4, it can be known that the intensity of the peaks increased as the content of retinol increased (FIG. 10).

Experimental Example 8: Test for Effect of ZIF-8-Nanocellulose Composite on Promoting Transdermal Absorption With the constitutional composition recited in Table 22, liposomes having the ZIF-8-nanocellulose composite containing 10% retinol (Liposome A) and general liposomes (Liposome B) were prepared, respectively.

TABLE 22

| Ingredient | Liposome A | Liposome B |
| --- | --- | --- |
| ZIF-8-nanocellulose composite containing 10% retinol | 10 | — |
| Saturated lecithin | 3 | 3 |
| Sodium stearoyl glutamate | 0.8 | 0.8 |
| Shea butter | 1 | 1 |
| Macadamia nut oil | 10 | 10 |
| Retinol | — | 1 |
| Distilled water | 75.2 | 84.2 |
| Total amount | 100 | 100 |

(Unit: % by weight)

The artificial skin, Neoderm (Tego Science, Korea) was mounted to a Franz-type diffusion cell (Lab Fine Instruments, Korea). 50 mM phosphate buffer (pH 7.4, 0.1M NaCl) was added to a receptor cell (5 ml) of the Franz-type diffusion cell. A diffusion cell was then mixed and diffused at 600 rpm, 32° C., and 50 µl of Liposome A and Liposome B, respectively, were added to donor cells. Absorption and diffusion were carried out according to the predetermined time, and the area of the skin where the absorption and diffusion were carried out was 0.64 cm². After finishing the absorption and diffusion of the active ingredient, the residues—which were not absorbed and remained on the skin—were cleaned with dried Kimwipes™ or 10 ml of ethanol. The skin in which the active ingredient was absorbed and diffused was homogenized by the use of a tip-type homogenizer, and retinol absorbed into the skin was then extracted with 4 ml of dichloromethane. The extract was then filtrated with a 0.45 µm nylon membrane filter. The content was measured by high-performance liquid chromatography with the following conditions, and the results are represented in Table 23.

TABLE 23

| | Transdermal absorption (µg) | Rate of increase |
| --- | --- | --- |
| Liposome A | 0.4004 | 15.64% |
| Liposome B | 0.2560 | — |

A) Column: C18 (4.6 × 200 mm, 5 µm)
B) Mobile phase: methanol:hexane = 2:1
C) Flow rate: 0.8 ml/min
D) Detector: UV 275 nm As can be seen from Table 23, in the present invention retinol—which is encapsulated in the ZIF-8-nanocellulose composite—can be efficiently delivered into the skin.

What is claimed is:
1. A transdermal delivery composite comprising a metal-organic framework, nanocellulose, and a cosmetically active ingredient;
   wherein the metal-organic framework is a zeolite imidazolate framework (ZIF)-8; and wherein an imine group of the ZIF-8 is combined with the nanocellulose.

2. The transdermal delivery composite according to claim 1, which comprises 0.01 to 20 parts by weight of the nanocellulose based on 10 parts by weight of the metal-organic framework.

3. The transdermal delivery composite according to claim 1, wherein the cosmetically active ingredient is one or more selected from the group consisting of a moisturizer, a whitening agent, an anti-wrinkle agent, a UV blocking agent, a hair growth promoter, vitamin or a derivative thereof, amino acid or peptide, an anti-inflammatory agent, an acne therapeutic agent, a microbicide, female hormone, a keratolytic agent and a natural product.

4. A cosmetic composition comprising the transdermal delivery composite according to claim 1.

5. The cosmetic composition according to claim 4, which comprises 1 to 60% by weight of the transdermal delivery composite.

6. A method for preparing a transdermal delivery composite comprising:
   i) adding a nanocellulose and a cosmetically active ingredient solution to a metal-organic framework solution;
   ii) treating the solution obtained in step (i) by stirring or sonication to form a composite; and
   iii) drying the composite obtained in step (ii);
   wherein the metal-organic framework is a zeolite imidazolate framework (ZIF)-8; and
   an imine group of the ZIF-8 is combined with the nanocellulose.

7. The method for preparing a transdermal delivery composite according to claim 6, wherein the concentration of the nanocellulose solution is 5 to 20% by weight.

8. The method for preparing a transdermal delivery composite according to claim 6, wherein the step (iii) is carried out by high-temperature vacuum drying at 60° C. or higher, or freeze-drying.

9. The method for preparing a transdermal delivery composite according to claim 6, which further comprises a step of washing the composite after the step (iii).

10. The method for preparing a transdermal delivery composite according to claim 9, wherein the washing is carried out by using ethanol.

* * * * *